United States Patent [19]

Hester, Jr.

[11] 4,141,902
[45] Feb. 27, 1979

[54] 1-HALOMETHYL-6-PHENYL-4H-s-[4,3-a][1,4]BENZODIAZEPINES

[75] Inventor: Jackson B. Hester, Jr., Galesburg, Mich.

[73] Assignee: The Upjohn Company, Kalamazoo, Mich.

[21] Appl. No.: 138,288

[22] Filed: Apr. 28, 1971

[51] Int. Cl.$^2$ .................. C07D 487/04; A61K 31/55
[52] U.S. Cl. ....................... 260/308 R; 260/239 BD; 260/239.3 D; 424/269
[58] Field of Search ................................. 260/308 R

[56] References Cited

FOREIGN PATENT DOCUMENTS 6916543  5/1970  Netherlands ..................... 260/308 R

*Primary Examiner*—Alton D. Rollins
*Attorney, Agent, or Firm*—Hans L. Berneis

[57] ABSTRACT

1-Substituted-6-phenyl-4H-s-triazolo[4,3-a][1,4]benzodiazepines of the formula II:

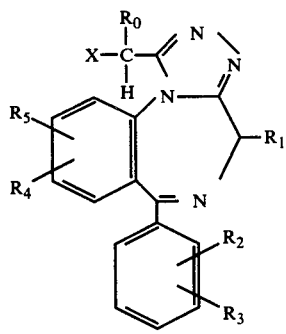

wherein $R_0$ is selected from the group consisting of hydrogen, methyl, ethyl, fluorine, chlorine, and bromine, and X is selected from fluorine, chlorine, and bromine; wherein $R_1$ is selected from the group consisting of hydrogen, alkyl of 1 to 3 carbon atoms inclusive; wherein $R_2$, $R_3$, $R_4$, and $R_5$ are selected from the group consisting of hydrogen, alkyl, as defined above, halogen, nitro, cyano, trifluoromethyl, and alkoxy, alkylthio, alkylsulfinyl, and alkylsulfonyl, in which the carbon chain moieties are of 1 to 3 carbon atoms, inclusive, are prepared by reacting a compound of the formula:

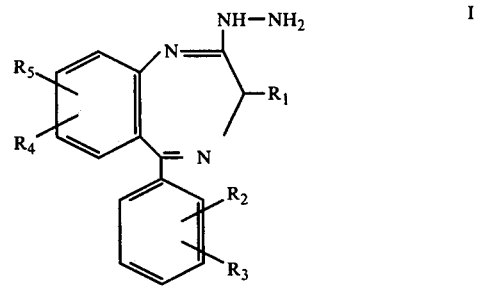

wherein $R_1$, $R_2$, $R_3$, $R_4$, and $R_5$ are defined as above, with an haloacyl chloride or haloacyl bromide of the formula

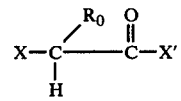

wherein $R_o$ and X are defined as above and X' is chlorine or bromine.

The new products of formula II including their pharmacologically acceptable acid addition salts are useful as sedatives, tranquilizers and muscle relaxants in mammals and birds, and if X=X"=Cl or Br they are useful as intermediates for cyano, alkylthio and dialkylamino products of high sedative and tranquilizing activity.

5 Claims, No Drawings

1-HALOMETHYL-6-PHENYL-4H-s-[4,3-a][1,4] BENZODIAZEPINES

BACKGROUND OF THE INVENTION

Field of the Invention

This invention is directed to new organic compounds and is particularly concerned with novel 1-substituted 6-phenyl-4H-s-triazolo[4,3-a][1,4]-benzodiazepines and a process for the production thereof.

The novel compounds and the process of production therefor can be illustratively represented as follows:

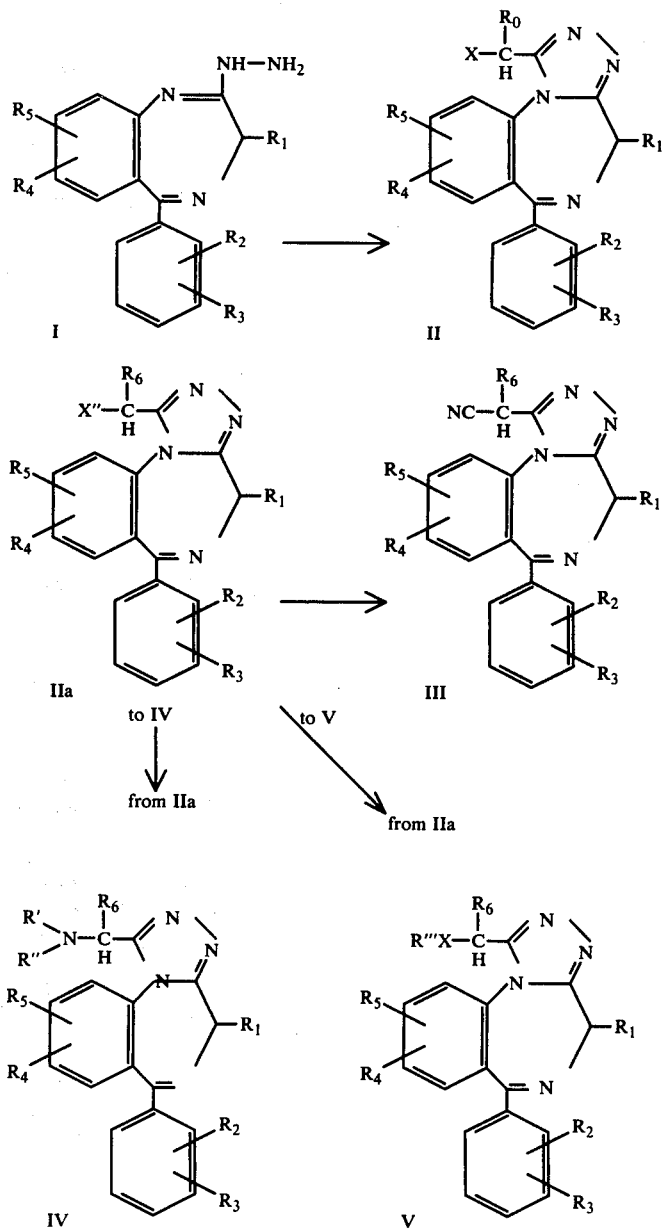

hydrogen, alkyl as defined above, halogen, nitro, cyano, trifluoromethyl, and alkoxy, alkylthio, alkylsulfinyl, and alkylsulfonyl, in which the carbon chain moieties are of 1 to 3 carbon atoms, inclusive, and wherein $R_6$ is hydrogen, methyl, or ethyl.

The process of this invention comprises: treating a selected 5-phenyl-3H-1,4-benzodiazepin-2-yl hydrazine (1) with a halo or dihalo acylhalide in a solvent in the presence of a base to give the corresponding 1-substituted-6-phenyl-4H-s-triazolo[4,3-a][1,4]benzodiazepine.

The 1-substituted compounds in which the substitutent is wherein $R_0$ is hydrogen, methyl, ethyl, chlorine, fluorine, or bromine; wherein X is fluorine, bromine or chlorine; wherein X" is bromine or chlorine; wherein R', R", and R''' are alkyl of 1 to 3 carbon atoms, inclusive, wherein $R_1$ is selected from the group consisting of hydrogen and alkyl defined as above, wherein $R_2$, $R_3$, $R_4$, and $R_5$ are selected from the group consisting of $$X-\underset{H}{\overset{R_6}{\underset{|}{C}}}-$$

wherein X is chlorine or bromine and $R_6$ is defined as above, can be treated with sodium cyanide to give the cyanide analogue (III); or it can be treated with a dialkylamine to give the 1-(dialkylamino)alkyl compound IV, or treated with a alkylmercaptan to give a 1-alkylthioalkyl compound (V).

DESCRIPTION OF THE PREFERRED EMBODIMENT

Lower alkyl groups of 1 to 3 carbon atoms, inclusive, are exemplified by methyl, ethyl, propyl, and isopropyl.

The carbon chain moiety of alkoxy, alkylthio, alkylsulfinyl alkylsulfonyl, is alkyl of 1 to 3 carbon atoms, inclusive, as defined above.

The term halogen includes fluorine, chlorine, and bromine.

The novel compounds of the formula II including acid addition salts thereof have sedative, tranquilizing and muscle relaxant effects in mammals and birds.

The acid addition salts of compounds of formula II contemplated in this invention, are the hydrochlorides, hydrobromides, hydroiodides, sulfates, phosphates, cyclohexanesulfamates, methanesulfonates, and the like, prepared by reacting a compound of formula II with the stoichiometrically calculated amount of the selected pharmacologically acceptable acid.

Sedative effects of 8-chloro-1-(chloromethyl)-6-phenyl-4H-s-triazolo[4,3-a][1,4]-benzodiazepine are shown by the following tests in mice:

Chimney test: [Med. Exp. 4, 11 (1961)]: The effective interperitoneal dosage for 50% of mice ($ED_{50}$) is 25mg/kg. The test determines the ability of mice to back up and out of a vertical glass cylinder within 30 seconds. At the effective dosage, 50% of the mice failed doing it.

Dish test: Mice in Petri dishes (10 cm. diameter, 5 cm. high, partially embedded in wood shavings), climb out in a very short time, when not treated. Mice remaining in the dish for more than 3 minutes indicates tranquilization. $ED_{50}$ equals the dose of test compound at which 50% of the mice remain in the dish. The $ED_{50}$ (intraperitoneal adminstration) in this test was 20 mg./kg.

Pedestal test: The untreated mouse leaves the pedestal in less than a minute to climb back to the floor of the standard mouse box. Tranquilized mice will stay on the pedestal for more than 1 minute. The $ED_{50}$ (intraperitoneal adminstration) is 20 mg./kg.

Nicotine antagonism test: Mice in a group of 6 are injected with the test compound [8-chloro-1-(chloromethyl)-6-phenyl-4H-s-triazolo[4,3-a][1,4]benzodiazepine]. Thirty minutes later the mice including control (untreated) mice are injected with nicotine salicylate (2mg./kg.). The control mice show over-stimulation, i.e., (1) running convulsions followed by (2) tonic extensor fits; followed by (3) death. An intraperitoneal dosage of 3.6 mg./kg. of the test compound protected 50% of the mice against (2) and (3).

Antagonism to strychnine (as sulfate): The effective dosage $ED_{50}$ of 8-chloro-1-(chloromethyl)-6-phenyl-4H-s-triazolo[4,3-a][1,4]benzodiazepine is 25 mg./kg. orally in mice. The test consists in orally administering into groups of 6 mice the test compound, 8-chloro-1-(chloromethyl)-6-phenyl-4H-s-triazolo[4,3-a][1,4]benzodiazepine and 30 minutes later 3mg./kg. strychnine sulfate intraperitoneally. The survivors after 4 hours reflect the activity of the compound as a muscle relaxant and antispasmodic. A dosage of 3 mg./kg. of strychnine sulfate is routinely fatal to all the control mice.

The following compounds have (by intraperitoneal injection) $ED_{50}$ as shown in the table below.

| COMPOUND | $ED_{50}$ (in mg./kg.) | | | |
|---|---|---|---|---|
| | Ch | D | P | Ni |
| 8-chloro-1-(dichloromethyl)-6-phenyl-4H-s-triazolo[4,3-a][1,4]benzodiazepine | 1.6 | 1.4 | 3.5 | 1.4 |
| 8-chloro-1-(α-chloroethyl)-6-phenyl-4H-s-triazolo[4,3-a][1,4]benzodiazepine | 4 | 0.8 | 4.5 | 0.9 |

Ch = Chimney test
D = dish test
P = pedestal test
Ni = nicotine antagonism (3) test The pharmaceutical forms contemplated by this invention include pharmaceutical compositions suited for oral, parenteral, and rectal use, e.g., tablets, powder packets, cachets, dragees, capsules, solutions, suspension, sterile injectable forms, suppositories, bougies, and the like. Suitable diluents or carriers such as carbohydrates (lactose), proteins, lipids, calcium phosphate, cornstarch, stearic acid, methylcellulose and the like may be used as carriers or for coating purposes. Oil, e.g., coconut oil, sesame oil, safflower oil, cottonseed oil, peanut oil may be used for preparing solutions or suspensions of the active drug. Sweetening, coloring and flavoring agents may be added.

For mammals and birds food premixes, with starch, oatmeal, dried fishmeat, fishmeal, flour and the like can be prepared.

As tranquilizers the compounds of formula II can be use in dosages of 0.5 mg. to 25 mg./kg. in oral or injectable preparations, as described above, to alleviate tension and anxiety in mammals, or birds, such as e.g., occurs when animals are in travel.

Other acid addition salts of the compounds of formula II can be made such as the fluosilicic acid addition salts which are useful mothproofing compounds or the trichloroacetates useful as herbicides against Johnson grass, Bermuda grass, yellow foxtail and green foxtail, and quack grass.

The starting materials of formula I of this invention, are prepared e.g. by reacting a 5-phenyl-3H-1,4-benzodiazepin 2-yl-thione with hydrazine and as further shown in preparation 1.

In carrying out the process of this invention a 5-phenyl-3H-1,4-benzodiazepin-2-yl hydrazine I is treated with an acyl halide

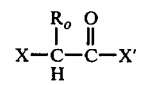

wherein $R_o$ is selected from the group consisting of hydrogen, methyl, ethyl, fluorine, chlorine, and bromine, wherein X is fluorine, chlorine, or bromine and X' is chlorine or bromine, at 15-30° C., for 1 to 3 hours. The reaction is preferably carried out in a solvent such as acetic or propionic acid. At the end of the reaction period at a temperature of 15-30° C. the reaction mixture is neutralized with sodium acetate, sodium carbonate or sodium bicarbonate and heated preferably to reflux. After refluxing for from 1 to 5 hours, the mixture is cooled and the product recovered and purified by conventional methods, such as neutralization of the reaction mixture, extraction, crystallization and chromatography. The product thus isolated is a 1-(haloalkyl)-6-phenyl-4H-s-triazolo[4,3-a][1,4]benzodiazepine (II).

If compound II is a 1-(α-monohaloalkyl)-6-phenyl-4H-s-triazolo[4,3-a][1,4]benzodiazepine in which the halogen is chlorine or bromine (IIa) it can be converted to a 1-(α-cyanoalkyl)compound III; or a 1-(α-dialkylaminoalkyl) compound IV or a 1-(α-alkylthioalkyl) compound V by a substitution reaction. For example IIa can be converted to III with an alkali metal cyanide such sodium or potassium cyanide in an organic solvent such as dimethylsulfoxide or dimethylformamide at a temperature of 25–100° C. In the preferred embodiment of this invention dimethylsulfoxide, sodium cyanide, in an amount of 5–15% over the stoichiometrically calculated amount and a temperature between 75–90° C. are used. The product III is recovered by conventional procedures such as extraction, chromatography and recrystallization.

The step IIa → IV is generally carried out by reacting a compound of formula IIa with dialkyamine with or without a solvent. If a solvent is used, such as tetrahydrofuran, dioxane, dimethylformamide, diethylformamide or a lower alkanol a catalyst such as sodium iodide can be used. The same catalyst, however, can also be used, when no specific solvent is used other than an excess of the dialkylamine. The reaction is carried out at temperatures of 25–125° C. for 6–19 hours. The product IV is recovered by conventional procedures e.g. extraction, recrystallization or chromatography.

The reaction 11a → V is carried out by allowing a compound of formula IIa to react with a lower alkyl thiol e.g. methyl, ethyl, propyl, or isopropyl thiol in the presence of a base, e.g. an alkali metal hydroxide, alkoxide or hydride such as sodium or potassium hydroxide, methoxide, or ethoxide, sodium hydride or potassium hydride and the like. Solvents, such as tetrahydrofuran, dioxane, dimethylformamide, diethylformamide, dimethylsulfoxide, or methanol, ethanol, isopropanol are preferably used, at 25–50° C. during 1 to 5 hours. The product V is recovered by conventional procedures e.g. extraction, recrystallization or chromatography.

The following examples and Preparation are illustrative of the processes and products of the present invention, but are not to be construed as limiting.

Preparation 1

7-Chloro-5-phenyl-3H-1,4-benzodiazepin-2-yl hydrazine

A stirred mixture of 7-chloro-1,3-dihydro-5-phenyl-2H-1,4-benzodiazepine-2-thione (50g, 0.174 mole) and methanol (1700 ml.) was treated with hydrazine hydrate (34.9 g.) and allowed to remain at ambient temperature for 1 hour 45 minutes. A slow stream of nitrogen was bubbled through the mixture during this period. The resulting solution was concentrated in vacuo at 25–30° C. The thus obtained residue was mixed with water and extracted with chloroform. The extract was dried over anhydrous potassium carbonate and concentrated under reduced pressure on the rotary evaporator in such a manner that the chloroform was replaced by ethyl acetate. The resulting mixture was crystallized at 4° C. ti give 26.6 g. of 7-chloro-5-phenyl-3H-1,4-benzodiazepin-2-yl hydrazine of melting point 184–186° C. and 3.04 g. of melting point 204–211° C. (60%). This compound decomposes on heating in solvents to an unknown product, melting point 261–262° C. The analytical sample was crystallized from ethyl acetate and had a melting point 217.5–219° C.

Anal. calcd. for $C_{15}H_{13}ClN_4$: C, 63.27; H, 4.60; Cl, 12.45; N, 19.68. Found: C, 63.30; H, 4.52; Cl, 12.46; N, 18.86.

The starting thiones of this invention, substituted or unsubstituted 1,3-dihydro-5-phenyl-2H-1,4-benzodiazepine-2-thiones, are described by G. A. Archer and L. H. Sternback [J. Org. Chem. 29, 231 (1964) and U.S. Pat. No. 3,422,091]. These compounds are made by the reaction of the known substituted or unsubstituted 1,3-dihydro-5-phenyl-2H-1,4-benzodiazepin-2-ones by heating with phosphorus pentasulfide in pyridine for about 45 minutes (Archer et al., ibid.).

EXAMPLE 1

8-Chloro-1-(chloromethyl)-6-phenyl-4H-s-triazolo[4,3-a][1,4]benzodiazepine

7-Chloro-5-phenyl-3H-1,4-benzodiazepin-2-yl hydrazine [14.2 g., 0.05 mole] was added slowly to acetic acid (150 ml.) with external cooling. A solution of chloroacetyl chloride (5.65 g.) in acetic acid (75 ml.) was then added during 10 minutes, and the red solution was stirred at ambient temperature for 1.5 hours treated with sodium acetate (4.1 g.), stirred again for 30 minutes and then refluxed for 3 hours and 15 minutes. This mixture was cooled, poured into ice water and concentrated to a small volume. It was then diluted with water, neutralized with sodium bicarbonate and extracted with chloroform. The extract was dried over anhydrous magnesium sulfate, concentrated and the residue chromatographed on silica gel (1 kg.) with 1% methanol-99% chloroform. The product obtained from the column was crystallized from EtOAc to give: 6.36 g. of 8-chloro-1-(chloromethyl)-6-phenyl-4H-s-triazolo[4,3-a][1,4]benzodiazepine. The analytical sample had a melting point 183–186.5° C.

Anal. calcd. for $C_{17}H_{12}Cl_2N_4$: C, 59.49; H, 3.53; Cl, 20.66; N, 16.33 Found: C, 59.59; H, 3.31; Cl, 20.21; N, 16.42.

EXAMPLE 2

8-Chloro-1-(dichloromethyl)-6-phenyl-4H-s-triazolo[4,3-a][1,4]benzodiazepine

7-Chloro-5-phenyl-3H-1,4-benzodiazepin-2-yl hydrazine (2.85 g., 0.01 mole) was added, under nitrogen with stirring and cooling to acetic acid (30 ml.) This mixture was treated dropwise at ambient temperature with a solution of dichloroacetyl chloride (1.47 g., 0.01 mole) in acetic acid (25 ml.), stirred for 1.5 hours, treated with sodium acetate (0.82 g., 0.01 mole), stirred for 30 minutes and refluxed for 4 hours. It was then cooled, poured into water and concentrated in vacuo to a small volume. This was neutralized with sodium bicarbonate and extracted with chloroform. The extract was washed with a dilute sodium chloride solution, dried over anhydrous magnesium sulfate and concentrated. The residue was crystallized from ether to give 1.95 g. (51.3%) of 8-chloro-1-(dichloromethyl)-6-phenyl-4H-s-triazolo[4,3-a][1,4]-benzodiazepine of melting point 193–196° d. C. The analytical sample was crystallized from methylene chloride-ethyl ether and had a melting point 196.5–198° C.

Anal. calcd. for $C_{17}H_{11}Cl_3N_4$: C, 54.06; H, 2.94; Cl, 28.17; N, 14.84. Found: C, 54.11; H, 2.97; Cl, 27.72; N, 15.00.

EXAMPLE 3

8-Chloro-1-(bromomethyl)-6-phenyl-4H-s-triazolo[4,3-a][1,4]benzodiazepine

In a manner given in Example 1, 7-chloro-5-phenyl-3H-1,4-benzodiazepin-2-yl hydrazine was reacted with bromoacetyl chloride and after 1.5 hours with sodium acetate, then refluxed to give 8-chloro-1-bromomethyl-6-phenyl-4H-s-triazolo[4,3-a][1,4]benzodiazepine.

EXAMPLE 4

8-Chloro-1-(α-chloroethyl)-6-phenyl-4H-s-triazolo[4,3-a][1,4]benzodiazepine

7-Chloro-5-phenyl-3H-1,4-benzodiazepin-2-yl hydrazine (2.85 g., 0.01 mole) was added, under nitrogen, with cooling and stirring to glacial acetic acid (30 ml.). A solution of 2-chloropropionyl chloride in acetic acid (15 ml.). was then added dropwise, and the resulting red solution was stirred at room temperature for 1.5 hours, treated with sodium acetate (0.82 g., 0.01 mole), stirred for an additional 30 minutes and then refluxed for 2 hours. This mixture was cooled, poured into ice water and concentrated to a small volume. The residual solution was neutralized with sodium bicarbonate and extracted with methylene chloride. The extract was dried over anhydrous magnesium sulfate and concentrated. The residue was chromatographed on silica gel (400 g.) with 1% methanol-99% chloroform. The product thus obtained was crystallized from a small amount of ethyl acetate to give 1.39 g. of 8-chloro-1-(α-chloroethyl)-6-phenyl-4H-s-triazolo[4,3-a][1,4]benzodiazepine of melting point 153.5°–156.5° C.

Anal. calcd. for $C_{18}H_{14}Cl_2N_4$: C, 60.52; H, 3.95; Cl, 19.85; N, 15.68 Found: C, 60.34; H, 4.07; Cl, 19.81; N, 15.65

EXAMPLE 5

8-Fluoro-1-(dibromomethyl)-6-(o-chlorophenyl)-4H-s-triazolo[4,3-a][1,4]benzodiazepine In the manner given in Example 2, 7-fluoro-5-(o-chlorophenyl)-3H-1,4-benzodiazepin-2-yl hydrazine was reacted with dibromoacetyl chloride and after 1.5 hours with sodium acetate, then the mixture was refluxed to give 8-fluoro-1-(dibromomethyl)-6-(o-chlorophenyl)-4H-s-triazolo-[4,3-a][1,4]benzodiazepine.

EXAMPLE 6

7,8-Dicyano-1-(α-chloroethyl)-6-(o-bromophenyl)-4H-triazolo[4,3-a][1,4]benzodiazepine In the manner given in Example 1, 6,7-dicyano-5-(o-bromophenyl)-3H-1,4-benzodiazepin-2-yl hydrazine was reacted with α-chloropropionyl chloride and after 1.5 hours with sodium acetate, then refluxed to give 7,8-dicyano-1-(α-chloroethyl)-6-(o-bromophenyl)-4H-s-triazolo[4,3-a][1,4]benzodiazepine.

EXAMPLE 7

8-Chloro-1-(chloromethyl)-6(o-chlorophenyl)-4H-s-triazolo[4,3-a][1,4]benzodiazepine In the manner given in Example 1, 7-chloro-5-(o-chlorophenyl)-3H-1,4-benzodiazepin-2-yl hydrazine was reacted with chloroacetyl bromide and after 1.5 hours with sodium acetate, then the mixture was refluxed to give 8-chloro-1-(chloromethyl)-6-(o-chlorophenyl)-4H-s-triazolo[4,3-a][1,4]benzodiazepine.

EXAMPLE 8

8,10-Dimethyl-1-(fluoromethyl)-6-[p-(methylthio)-phenyl]-4H-s-triazolo[4,3-a][1,4]benzodiazepine In the manner given in Example 1, 7,9-dimethyl-5-[p-(methylthio)phenyl]-3H-1,4-benzodiazepin-2-yl hydrazine was reacted with fluoroacetyl bromide and after 1.5 hours with sodium acetate, then the mixture was refluxed to give 8,10-dimethyl-1-(fluoromethyl)-6-[p-(methylthio)phenyl]-4H-s-triazolo[4,3-a][1,4]benzodiazepine.

EXAMPLE 9

8-Chloro-1-(α-fluoroethyl)-6-(2,6-difluorophenyl)-4H-s-triazolo[4,3-a][1,4]benzodiazepin In the manner give in Example 1, 7-chloro-5-(2,6-difluorophenyl)-3H-1,4-benzodiazepin-2-yl hydrazine was reacted with α-fluoropriopionyl chloride and after 1.5 hours with sodium acetate, then the mixture was refluxed to give 8-chloro-1-(α-fluoroethyl)-6-(2,6-difluorophenyl)-4H-s-triazolo[4,3-a][1,4]benzodiazepine.

EXAMPLE 10

8-Nitro-1-(bromomethyl)-6-(o-chlorophenyl)-4H-s-triazolo[4,3-a][1,4]-benzodiazepine In the manner given in Example 1, 7-nitro-5-(o-chlorophenyl)-3H-1,4-benzodiazepin-2-yl hydrazine was reacted with bromoacetyl bromide and after 1.5 hours with sodium acetate, then refluxed to give 8-nitro-1-(bromomethyl)-6-(o-chlorophenyl)-4H-s-triazolo[4,3-a][1,4]benzodiazepine.

EXAMPLE 11

1-Dichloromethyl-7-trifluoromethyl-9-propylsulfonyl-6-(p-ethoxyphenyl)-4H-s-triazolo[4,3-a][1,4]benodiazepine In the manner given in Example 1, 6-trifluoromethyl-8-propylsulfonyl-5-(p-ethoxyphenyl)-3H-1,4-benzodiazepin-2-yl hydrazine was reacted with dichloroacetyl chloride and after 1.5 hours with sodium acetate, then refluxed to give 1-(dichloromethyl)-7-trifluoromethyl-9-propylsulfonyl-6-(p-ethoxyphenyl)-4H-s-triazolo[4,3-a][1,4]benzodiazepine.

EXAMPLE 12

8-Chloro-6-phenyl-4H-s-triazolo[4,3-a][1,4]benzodiazepine-1-acetonitrile

To a stirred solution of sodium cyanide (0.108 g.; 0.0022 mole) in dry dimethylsulfoxide (2.4 ml.) was added, under nitrogen and with stirring, 8-chloro-1-(chloromethyl)-6-phenyl-4H-s-triazolo[4,3-a][1,4]benzodiazepine (0.686 g.; 0.002 mole) in a bath maintained at 84° C. An immediate red solution resulted. After 28 minutes the mixture was cooled, and poured into water: the crude product was extracted with chloroform. The extracts were washed with brine solution, dried over anhydrou potassium carbonate and concentrated to give a residue which was recrystallized from ethyl acetate-Skellysolve B hexanes, [decolorizing the solution with activated charcoal (Darco)], to give 0.214 g. of 8-chloro-6-phenyl-4H-s-triazolo-[4,3-a][1,4]benzodiazepine-1-acetonitrile of melting point 199.5°–200.5° C. The analytical sample had a melting point of 198° C.

Anal. calcd. for $C_{18}H_{12}ClN_5$: C, 64.77; H, 3.63; Cl, 10.62; N, 20.98. Found: C, 64.52; H, 3.86; Cl, 10.51; N, 20.95.

In the same manner 1-bromomethyl-8-chloro-6-phenyl-4H-s-triazolo[4,3-a][1,4]benzodiazepine can be condensed with potassium cyanide in dimethylsulfoxide to give 8-chloro-6-phenyl-4H-s-triazolo[4,3-a][1,4]benzodiazepine-1-acetonitrile.

EXAMPLE 13

8-Chloro-1-[)diethylamino)methyl]6-phenyl-4H-s-triazolo[4,3-a][1,4]benzodiazepine 8-Chloro-1-(chloromethyl)-6-phenyl-4H-s-triazolo[4,3-a][1,4]benzodiazepine (343 mg., 0.001 mole) was added to solution of diethylamine (1 ml.) in dry dimethylformamide (5 ml.) and the mixture was stirred at ambient temperature under nitrogen, for 4 hours 30 minutes. Sodium iodide (50 mg.) was added and the mixture was stirred at ambient temperature for 17 hours 30 minutes and heated at 100°–111° C. for 6 hours. It was then poured into ice water and extracted witch chloroform. The extract was washed with water, dried over anhydrous potassium carbonate and concentrated in vacuo. The residue was crystallized from ethyl acetate-Skellysolve B hexanes to give 0.277 g. of 8-chloro-1-[(diethylamino)methyl)-6-phenyl-4H-s-triazolo[4,3-a][1,4]benzodiazepine of melting point 128.5°–131.5° C. The analytical sample had a melting point of 131.5°–132.5° C.

Anal. calcd. for $C_{21}H_{22}ClN_5$: C, 66.39; H, 5.84; Cl, 9.33; N, 18.44. Found: C, 66.20; H, 6.06; Cl, 9,29; N, 18.55.

In the manner given in Example 13, 8-chloro-1-[(dimethylamino) or (dipropylamino)methyl]-6-phenyl-4H-s-triazolo[4,3-a][1,4]benzodiazepines are prepared by reacting a dimethylamine or dipropylamine with 8-chloro-1-(chloromethyl)-6-phenyl-4H-s-triazolo[4,3-a][1,4]benzodiazepine.

EXAMPLE 14

8-Chloro-1-(ethylthio)-6-phenyl-4H-s-triazolo[4,3-a][1,4]benzodiazepine

A solution of 8-chloro-1-(chloromethyl)-6-phenyl-4H-s-triazolo[4,3-a][1,4]benzodiazepine in tetrahydrofuran was heated to 50° C. and thereto was added ethylmercaptan in dioxane and sodium hydroxide in ethanol. The heating was continued for four hours, the mixture was then cooled, poured into water and extracted with chloroform. The chloroform extracts were dried over anhydrous potassium carbonate, evaporated in vacuo and the resulting residue crystallized and recrystallized from ethyl acetate-Skellysolve B hexanes to give 8-chloro-1-(ethylthio)-6-phenyl-4H-s-triazole[4,3-a][1,4]benzodiazepine.

EXAMPLE 15

8-Trifluoromethyl-1-(propylthio)-6-(o-chlorophenyl)-4H-s-triazolo[4,3-a][1,4]benzodiazepine In the manner given in Example 14, a solution of 8-trifluoromethyl-1-(chloromethyl)-6-(o-chlorophenyl)-4H-s-triazolo[4,3-a][1,4]benzodiazepine was heated with propanethiol and sodium hydroxide to give 8-trifluoromethyl-1-(propylthio)-6-(o-chlorophenyl)-4H-s-triazolo[4,3-a][1,4]benzodiazepine.

The novel compounds of formula II and the compounds of formulae III, IV, and V can be reacted with selected acids, e.g. hydrochloric, hydrobromic, sulfuric, phosphoric, tartaric, citric, lactic, cyclohexanesulfamic, toluenesulfonic and other acids to give the corresponding pharmaceutically acceptable acid addition salts. This reaction is carried out under conventional conditions, in solvents such as ether, dioxane, tetrahydrofuran and the like at room temperatures, and the resulting precipitate salts are collected by filtration. These salts can be used in place of the free base for the same pharmaceutical purpose described before.

I claim:

1. A 1-substituted-6-phenyl-4H-s-triazolo[4,3-a][1,4]benzodiazepine of the formula II:

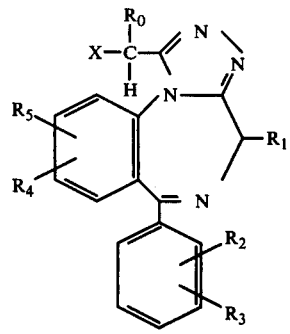

wherein $R_0$ is selected from the group consisting of hydrogen, methyl, ethyl, fluorine, chlorine, and bromine; wherein X is fluorine, bromine, or chlorine; wherein $R_1$ is selected from the group consisting of hydrogen and alkyl of 1 to 3 carbon atoms, inclusive; and wherein $R_2$, $R_3$, $R_4$, and $R_5$ are selected from the group consisting of hydrogen, alkyl as defined above, halogen, nitro, cyano, trifluoromethyl, and alkoxy, alkylthio, alkylsulfinyl, and alkylsulfonyl, in which the carbon chain moieties are of 1 to 3 carbon atoms, inclusive and the pharmaceutically acceptable acid addition salts thereof.

2. A compound according to claim 1 wherein $R_0$, $R_1$, $R_2$, $R_3$, and $R_5$ are hydrogen, $R_4$ is 8-chloro, X is chloro and the compound is therefore 8-chloro-1-(chloromethyl)-6-phenyl-4H-s-triazolo[4,3-a][1,4]benzodiazepine 3. A compound according to claim 1 wherein $R_0$, $R_1$, $R_2$, $R_3$, and $R_5$ are hydrogen, X is bromo, $R_4$ is 8-chloro, and the compound is therefore 8-chloro-1-(bromomethyl)-6-phenyl-4H-s-triazolo-[4,3-a][1,4]benzodiazepine.

4. A compound according to claim 1 wherein X and $R_0$ are chloro, $R_4$ is 8-chloro and $R_1$, $R_2$, $R_3$, and $R_5$ are hydrogen, and the compound is therefore 8-chloro-1-(dichloromethyl)-6-phenyl-4H-s-triazolo[4,3-a][1,4]benzodiazepine.

5. A compound according to claim 1 wherein X is chloro, $R_0$ is methyl, $R_4$ is 8-chloro and $R_1$, $R_2$, $R_3$, and $R_5$ are hydrogen, and the compound is therefore 8-chloro-1-(α-chloroethyl)-6-phenyl-4H-s-triazolo[4,3-a][1,4]benzodiazepine.

* * * * *